(12) United States Patent
Fraenkel et al.

(10) Patent No.: US 8,612,160 B2
(45) Date of Patent: Dec. 17, 2013

(54) IDENTIFYING BIOLOGICAL RESPONSE PATHWAYS

(75) Inventors: Ernest Fraenkel, Cambridge, MA (US); Shao-Shan Carol Huang, Cambridge, MA (US); David R. Karger, Cambridge, MA (US); Laura Riva, Cambridge, MA (US); Esti Yeger-Lotem, Misgav (IL)

(73) Assignee: Massachusetts Institute of Technology, Cambridge, MA (US)

( * ) Notice: Subject to any disclaimer, the term of this patent is extended or adjusted under 35 U.S.C. 154(b) by 620 days.

(21) Appl. No.: 12/618,915

(22) Filed: Nov. 16, 2009

(65) Prior Publication Data

US 2010/0250143 A1    Sep. 30, 2010

Related U.S. Application Data

(60) Provisional application No. 61/114,783, filed on Nov. 14, 2008.

(51) Int. Cl.
*G06F 19/00* (2011.01)
*G06F 19/12* (2011.01)

(52) U.S. Cl.
USPC .......................................................... 702/19

(58) Field of Classification Search
None
See application file for complete search history.

(56) References Cited

PUBLICATIONS

Shannon et al. (Genome Research (2003) vol. 13, pp. 2498-2504).*
Dittrich et al. (Bioinformatics (2008) vol. 24, No. 13, July; pp. i223-i231).*
Ideker et al. Bioinformatics (2002) vol. 18, Suppl. 1, pp. S233-S240.*
Lan et al. Nucleic Acids Research (2011) vol. 39, pp. W424-W429.*
Canuto et al. Networks (2001) vol. 38, No. 1, pp. 50-58.*
Schmidt et al. Seventh International Conference on Intelligent Systems Design and Applications (2007) IEEE Computer Society, pp. 271-276.*
Ljubić, et al. "An Algorithmic Framework for the Exact Solution of the Prize-Collecting Steiner Tree Problem" *Vienna University of Technology*. (2006) 25 pages.

* cited by examiner

*Primary Examiner* — Lori A Clow
(74) *Attorney, Agent, or Firm* — Occhiuti & Rohlicek LLP

(57) ABSTRACT

A method for identifying a mechanism associated with a cellular response includes identifying molecules participating in the cellular response; accessing a database containing information characterizing molecular interactions; determining pathways connecting the identified molecules participating in the cellular response; and solving an optimization problem that includes determining a subset of the molecules and interactions having a minimum aggregate cost. The pathways include, nodes, each representing a molecule, and edges, each connecting a respective pair of nodes and representing an interaction between a respective pair of molecules represented by the respective pair of nodes. Nodes from a subset of nodes represent molecules identified as participating in the cellular response.

11 Claims, 3 Drawing Sheets

IDENTIFYING BIOLOGICAL RESPONSE PATHWAYS

RELATED APPLICATIONS

This application claims the benefit of the priority date of U.S. Provisional Application 61/114,783, filed on Nov. 14, 2008, the contents of which are herein incorporated by reference in their entirety.

STATEMENT AS TO FEDERALLY SPONSORED RESEARCH

This invention was made with Government support under Grant Nos. P01 CA042063 and U54 CA112967, awarded by the NIH and Grant No. CCF-0635286, awarded by the NSF. The Government has certain rights in this invention.

FIELD OF INVENTION

This disclosure relates to systems and methods for identification of biological response pathways and networks, including, for example, pathways for signaling events.

BACKGROUND

Biological signal transduction involves biochemical, biophysical, and/or biomechanical processes by which a cell converts one type of signal into another. In the course of such transduction, a cell typically senses and responds to an external stimulus (such as a hormone). This often initiates a sequence of biochemical reactions associated with various types of molecules present in the cell. Examples of such molecules include receptors, second messengers, enzymes, transcription factors, DNAs, and mRNAs.

The task of finding the relevant signaling pathways and the network of molecular interactions responsible for a particular signaling event can be a difficult one.

SUMMARY

In one aspect, the invention features a method for updating a computer-readable data storage medium with the aid of a particular microprocessor tied to the computer-readable data storage medium, the data storage medium containing interaction data, the interaction data being representative of interactions within a cell. Such a method includes receiving a global measurement of activity in a cell; causing the microprocessor to retrieve, from a database stored on a computer-readable medium, the interaction data, the interaction data including data representative of a subset of interactions within the cell, each of the interactions within that subset being consistent with the global measurement; causing the microprocessor to determine an aggregate cost for each of the interactions; causing the microprocessor to determine which of the interactions from the subset of interactions has a minimum aggregate cost; causing the microprocessor to provide output representative of the minimum cost interaction; and causing the output to be stored in the computer-readable data storage medium.

Some practices include representing the data from the database as an interactome. The interactome has nodes representing molecules, and edges connecting pairs of the nodes. Each edge represents an interaction between molecules represented by the nodes. Among these practices are those in which each node is weighted by a "node cost" representing an anticipated performance of a molecule associated with the node during a signaling event, and each edge is weighted by an "edge cost" representing a reliability of an interaction between molecules connected by the edge. Also among these practices are those in which causing the microprocessor to determine which of the signaling pathways from the subset of signaling pathways has a minimum aggregate cost comprises solving a PCST problem associated with the interactome to identify the pathways.

In another aspect, the invention includes a method for operating a machine for identifying a mechanism associated with a cellular response with the aid of a digital computer. These cellular responses include, but are by no means limited to signaling events, metabolic events, and phenotypic responses to a stimulus or stimuli.

Such a method includes identifying molecules participating in the cellular response; causing the computer to access a database containing information characterizing molecular interactions; and causing the computer to determine pathways connecting the identified molecules participating in the cellular response. The pathways include: a plurality of nodes, each node representing a molecule, and a plurality of edges, each edge connecting a respective pair of nodes and representing an interaction between a respective pair of molecules represented by the respective pair of nodes. The plurality of nodes includes a subset of nodes that represent molecules identified as participating in the cellular response. The method further includes causing the computer to solve an optimization problem that includes determining a subset of the molecules and interactions having a minimum aggregate cost.

In at least one practice, causing the microprocessor to determine pathways connecting the identified molecules participating in the cellular response includes: numerically processing data representing the network of potential interactions to determine a sub-network of nodes and edges representative of a response pathway between the input and the output.

In another practice, causing the microprocessor to solve an optimization problem includes: associating each node that participates in the cellular response with a penalty value; associating each edge with a cost value; forming an objective function based on the penalty values and the cost values; and identifying the sub-network of nodes and edges that minimizes a value of the objective function.

In still another practice, causing the microprocessor to solve an optimization problem includes: identifying one subset of the originally identified nodes as an input subset containing input nodes and a separate subset of the originally identified nodes as an output subset containing output nodes; identifying a source node representing a source of flow; identifying a destination node representing a destination of flow; associating a quantity of flow with the source of flow; associating each edge with a cost value; and forming an objective function for the optimization problem based on the cost values of the edges connecting the input and output nodes and the quantity of flow traversing these edges from the source node to the destination node.

Additional practices include those in which identifying molecules participating in a cellular response includes identifying one or more proteins from a group of consisting of phosphorylated proteins; proteins encoded by a gene that, when deleted, causes a change in an organism's phenotype; and proteins that are present in an amount that changes during a cellular response.

In some practices, the cellular response is a signaling event and the destination node represents a target gene of the signaling event.

Alternative practices include identifying the destination node according to measurements of differential gene expression associated with the signaling event.

Also among the alternative practices are those in which the pathways further include one or more intermediate nodes between the source node and the destination node, and those in which the pathways further include one or more intermediate nodes between the nodes participating in the cellular response A variety of molecules participating in the cellular response can be identified. Among these are proteins, mRNAs, DNA sequences, and protein-protein complexes.

In some embodiments, each edge is associated with a value that represents a degree of interaction between respective molecules represented by the pair of nodes connected by the edge.

In yet another aspect, the invention includes a tangible computer-readable medium having encoded thereon software for carrying out any of the foregoing methods.

Another aspect of the invention includes a data processing system configured to execute any of the foregoing methods. Such configuration can be achieved by programming a general purpose computer, thereby transforming that computer into a new special purpose machine that is structurally different from a computer without such programming. Or, configuration can be achieved by constructing an application specific integrated circuit for carrying out the foregoing methods.

Other features and advantages of the invention are apparent from the following description, from the claims, and from the attached figures in which:

DETAILED DESCRIPTION

Figure 1:
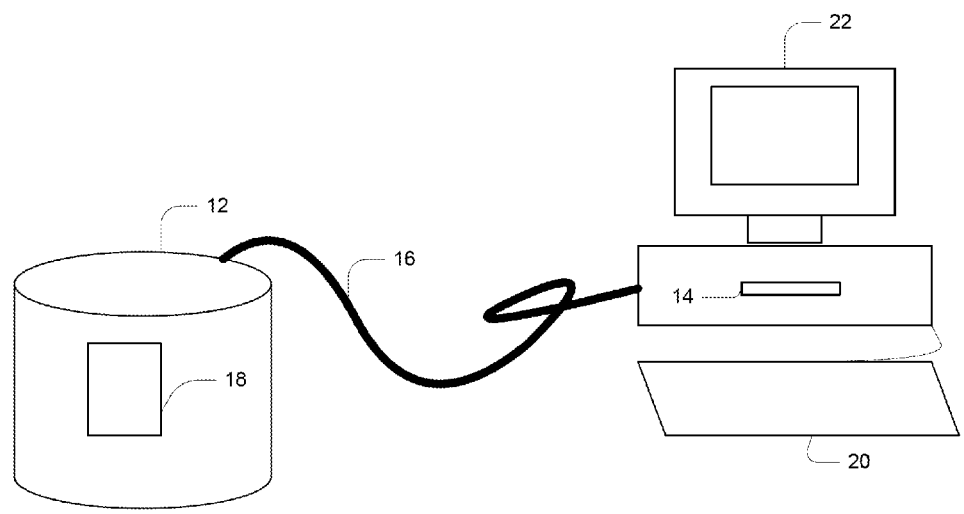
FIG. 1 shows a system for carrying out the method disclosed herein.

One method for identifying signaling pathways and for measuring characteristics of biological networks includes a computational approach that couples mathematical modeling with experimental data.

One computational approach applies differential equations to model detailed biophysical processes for making quantity predictions. A network of biophysical processes, for example, can be modeled with a set of coupled differential equations, each equation describing the reaction kinetics of the constituents (e.g., molecules) of a process. The parameters used in one differential equation may depend on the dynamic characteristics (e.g., the concentration) of other substances or processes within the cell.

A disadvantage to the foregoing computational method is that modeling large networks of highly-crossed interactions may require extensive knowledge about the connectivity of the network and the kinetic parameters of individual interactions. These may not always be available in many systems.

Another computational approach uses statistical learning methods to extract relationships between molecules and interactions based on a dataset of formerly identified signaling events/networks.

A disadvantage of the foregoing method is that it may not be suitable in those applications in which the dataset is small and appears in high dimensions. In addition, the relationships extracted by statistical learning are probabilistic in nature, and may not reflect the important mechanistic information of molecular interactions. Further, in cases where experimental observations are influenced by hidden variables, learning these variables can be difficult.

One embodiment of the systems and methods described herein uses a constraint optimization framework for identification of cellular signaling networks, as described in detail in Appendix A of U.S. Provisional Application 61/114,783.

As described in Appendix A, global measurements of a cell associated with a particular signaling event (e.g., the mating response of baker's yeast Saccharomyces cerevisiae to pheromone) are obtained and integrated into a mathematical model of molecular networks to identify one or more sequences of interactions involved in the signaling pathway relevant to this event. Here, the signaling pathway may include a cascade of molecules from cell-surface receptors, proteins, enzymes, transcription factors, genetic sequences, and possibly other molecules. Global measurements of the cell may include, for example, phosphoproteomic data from mass spectrometry and transcriptional profiling by microarray.

The mathematical model of molecular networks can be formed, for example, using experimentally determined protein-protein and/or protein-DNA interactions from biological databases such as BioGRID and MIPS, in conjunction with the experimental evidence for each interaction.

One way to model a network is to use an interactome graph having a set of nodes connected by edges. Each node represents a molecule. An edge connecting a pair of nodes represents the interaction of a pair of molecules corresponding to those nodes.

Each node can be weighted, for example, based on an anticipated importance of this node involved in a particular event. Additionally, each edge can also be weighted, for example, based on the reliability of the interaction represented by the edge. A detailed description of the formulation of a graph is provided in Appendix B of U.S. Provisional Application 61/114,783.

One way to identify a sequence or sequences of interactions relevant to the signaling event uses a constrained optimization approach described in detail in Appendix C of U.S. Provisional Application 61/114,783. Briefly, using a Prize Collecting Steiner Tree (PCST) model, the global measurements of the cell associated with the signaling event are imposed as constraints of the optimization process, and the solution of this process reveals the set of interactions that best satisfy the constrains. One optimization technique suitable for use here is described by Ljubic, et al., in *An Algorithmic Framework for the Exact Solution of the Prize-Collecting Steiner Tree Problem*, published in Mathematical Programming, Volume 105, Numbers 2-3, February 2006, the contents of which are incorporated herein by reference.

One example of using the above described techniques to identify the signaling pathway of the yeast pheromone response is illustrated in detail in Appendix B of U.S. Provisional Application 61/114,783. The reconstructed network of interactions relevant to this yeast pheromone response provides many features and advantages, some of which are described in detail below.

At the global level, the network is partitioned into highly coherent sub-networks that are functionally relevant to the biological processes associated with this response. Also, most of the connected proteins in each sub-network form complexes of defined functions. Further, a set of intermediate nodes that are not identified in the global measurements are revealed in the reconstructed network. These intermediate nodes are associated with genes implicated in mating defects and alternation in mating gene reporter expression. This suggests that the constraints imposed by the global measurements provide valuable information to guide the selection of important players that contribute to the response.

At the local level, the reconstructed pheromone signaling network resembles the known pathway. Other yeast MAPK pathways such as the PKC pathway and the filamentous growth pathway are also identified in the network.

At the transcription level, phosphorylated proteins appear highly informative in selecting interacting transcription factors. This is useful in understanding the condition-specific combinatorial control by transcription factors.

Appendices A-G of U.S. Provisional Application 61/114,783 provide examples of potential features and implementations for various embodiments and portions of embodiments.

The techniques described herein can be implemented as software tangibly embodied in an information carrier, e.g., in a machine-readable storage device for execution by, or to control the operation of data processing apparatus, e.g., a programmable processor, a computer, or multiple computers. Such software can be expressed in any form of programming language, including compiled or interpreted languages, and can be deployed in any form, including as a stand-alone program or as a module, component, subroutine, or other unit suitable for use in a computing environment.

FIG. 1 shows a particular computer-readable data storage medium 12 tied to a microprocessor 14 via a data communication path 16. The data storage medium stores information 18 representative of signaling pathways.

An input device 20 in communication with a processing element provides a way to control the microprocessor 14, and an output device 22 in communication with the microprocessor 14 provides tangible output for inspection, or a pathway for communicating with the data storage medium 12 to which the microprocessor 14 is tied.

In operation, the microprocessor 14 causes transformations to various electronic components within it, including transistors, diodes and resistors. Ultimately, the microprocessor 14 causes a physically measurable transformation of matter within the data storage medium 12 to which it is tied. This transformation is physically measurable since if it were not, there would be no way to read the data once it had been written.

Such software can be tied to a particular computer or to multiple particular computers at one site or distributed across multiple sites and interconnected by a communication network. Accordingly, such software can be deployed at or executed by a particular computer or on multiple particular computers at one site or distributed across multiple sites and interconnected by a communication network.

Figure 2:
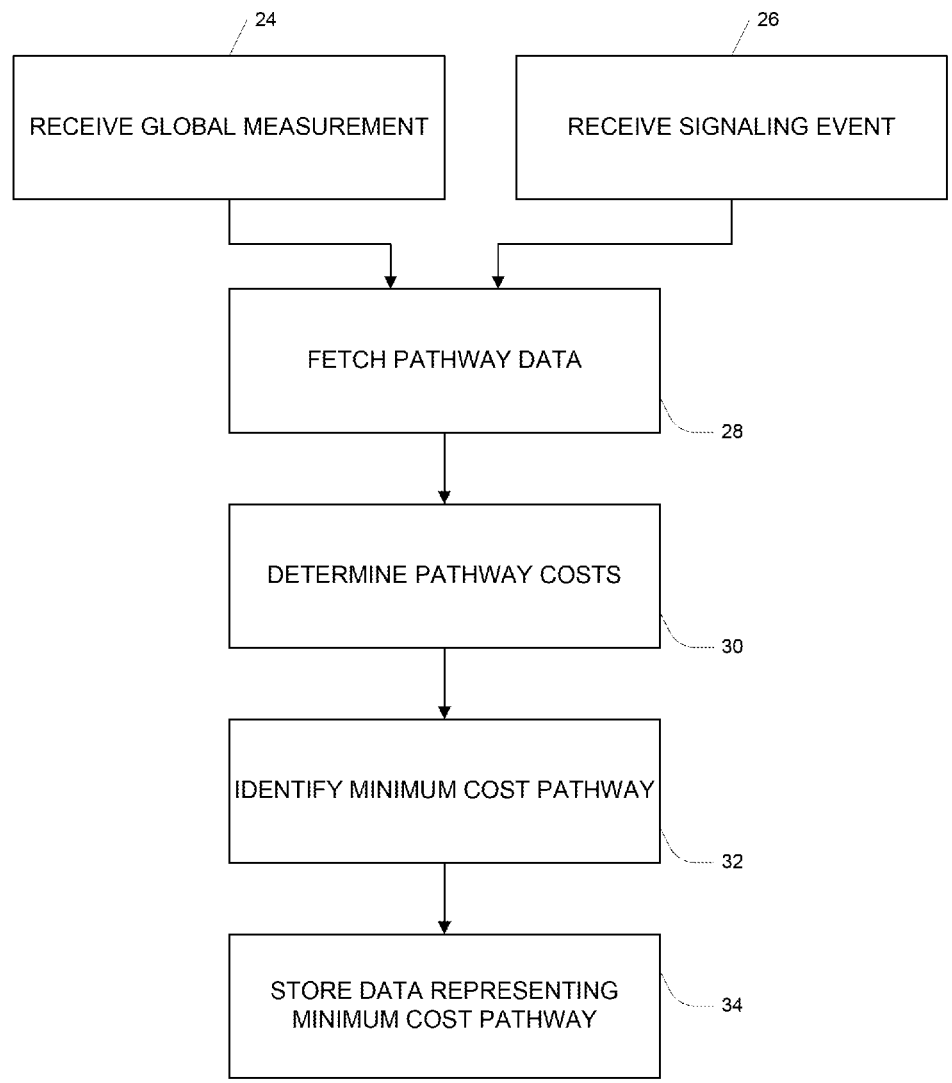
FIGS. 2 and 3 are flowcharts showing procedures carried out by the system shown in FIG. 1.

Referring to FIG. 2, the system receives global measurement data representing activity within a cell (step 24). The system then retrieves data representing the various interactions within the cell (step 28). Some of the stored data is consistent with the global measurement, and some of it is not. In some cases, both kinds of data are retrieved, and the two kinds of data are classified after retrieval. In other cases, only the data that is consistent with the global measurement is retrieved.

The system determines the aggregate costs of the individual interactions (step 30) and identifies, or determines, which interaction has the minimum aggregate cost (step 32). Finally, the system provides output representing the minimum cost interaction (step 34) and stores data representing that interaction in a computer-readable data storage medium (step 36).

Figure 3:
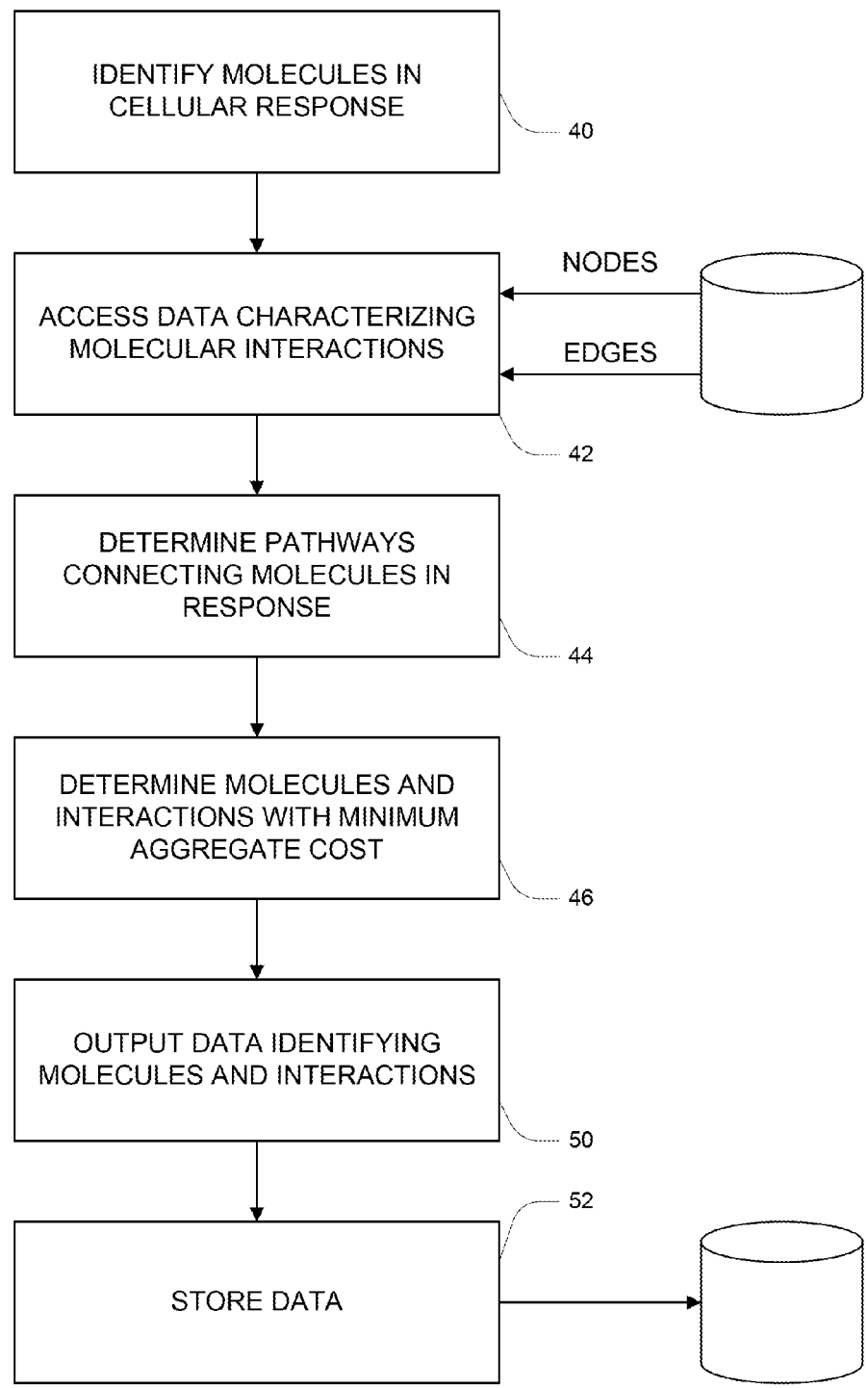

Referring now to FIG. 3, an alternative method includes first identifying those molecules that participate in a cellular response (step 40). Then, data characterizing interactions between molecules is retrieved (step 42). This data includes nodes representing the participating molecules and edges that connect these nodes. Weights associated with the edges represent the extent of interaction between molecules connected by that edge. Once this data is retrieved, one can determine which subset of molecules and interactions have a minimum aggregate cost (step 46). Data identifying such molecules and interactions can then be output (step 50) and stored on a computer-readable medium (step 52).

Functions can be distributed over a number of different components, for example, centralized on a single server. For example, a researcher may use a web-based interface to operate a program configured for identifying signaling pathways for cellular events. Data representing the results of the operation may be presented to the research in a printed form or in an electronic form (e.g., displayed on a computer screen).

To provide for interaction with a user, the techniques described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element, for example, by clicking a button on such a pointing device). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While the methods disclosed herein can be implemented on a general purpose digital computer, it is also possible to implement the methods on an application specific integrated circuit. In addition, it is possible to It is to be understood that the enclosed appendices and the foregoing description are intended to illustrate and not to limit the scope of the invention.

Having described the invention, and a preferred embodiment thereof, what is claimed as new and secured by Letters Patent is:

1. A method for updating a computer-readable data storage medium with the aid of a particular microprocessor tied to said computer-readable data storage medium, said data storage medium containing interaction data, said interaction data being representative of interactions within a cell, said method comprising: providing said microprocessor with a global measurement of activity in a cell, causing said microprocessor to retrieve, from a database stored on a computer-readable medium, said interaction data, said interaction data including data representative of a subset of interactions within the cell, each of said interactions being consistent with said global measurement, causing said microprocessor to determine an aggregate cost for each of said interactions, causing said microprocessor to determine which of said interactions from said subset of interactions has a minimum aggregate cost, causing said microprocessor to provide output representative of said minimum cost interaction, and causing said output to be stored in said computer-readable data storage medium, and representing said data from said database as an interactome, said interactome having nodes representing molecules, and edges connecting pairs of said nodes, each edge representing an interaction between molecules represented by said nodes, wherein causing said microprocessor to determine which of said signaling pathways from said subset of signaling pathways has a minimum aggregate cost comprises solving a prize-collecting Steiner tree problem associated with said interactome to identify said pathways.

2. The method of claim 1, wherein each node is weighted by a node cost representing an anticipated performance of a molecule associated with said node during a signaling event, and wherein each edge is weighted by an edge cost representing a reliability of an interaction between molecules connected by said edge.

3. A method for operating a machine for identifying a mechanism associated with a cellular response with the aid of a digital computer, the method comprising identifying molecules participating in the cellular response, causing the computer to access a database containing information characterizing molecular interactions, causing the computer to determine pathways connecting the identified molecules participating in the cellular response, wherein the pathways include a plurality of nodes, each node representing a molecule, and a plurality of edges, each edge connecting a respective pair of nodes and representing an interaction between a respective pair of molecules represented by the respective pair of nodes, wherein the plurality of nodes includes a subset of nodes that represent molecules identified as participating in the cellular response, and causing said computer to solve an optimization problem that includes determining a subset of the molecules and interactions having a minimum aggregate cost, wherein causing said microprocessor to solve an optimization problem includes identifying one subset of the originally identified nodes as an input subset containing input nodes and a separate subset of the originally identified nodes as an output subset containing output nodes, identifying a source node representing a source of flow, identifying a destination node representing a destination of flow, associating a quantity of flow with the source of flow, associating each edge with a cost value, and forming an objective function for said optimization problem based on the cost values of the edges connecting the input and output nodes and the quantity of flow traversing these edges from the source node to the destination node.

4. The method of claim 3, wherein causing said microprocessor to determine pathways connecting the identified molecules participating in the cellular response includes numerically processing data representing the network of potential interactions to determine a sub-network of nodes and edges representative of a response pathway between the input and the output.

5. The method of claim 3, wherein identifying molecules participating in a cellular response includes identifying one or more proteins selected from the group consisting of phosphorylated proteins, proteins encoded by a gene that, when deleted, causes a change in an organism's phenotype, and proteins that are present in an amount that changes during a cellular response.

6. The method of claim 3, wherein the cellular response is a signaling event and wherein the destination node represents a target gene of the signaling event.

7. The method of claim 6, further comprising identifying the destination node according to measurements of differential gene expression associated with the signaling event.

8. The method of claim 3, wherein the pathways further include one or more intermediate nodes between the source node and the destination node.

9. The method of claim 3, wherein identifying molecules participating in the cellular response comprises identifying molecules selected from the group consisting of proteins, mRNAs, DNA sequences, and protein-protein complexes.

10. The method of claim 3, wherein each edge is associated with a value that represents a degree of interaction between respective molecules represented by the pair of nodes connected by the edge.

11. The method of claim 3, wherein the cellular response is selected from the group consisting of a signaling event, a metabolic event, and a phenotypic response to a stimulus.

* * * * *